United States Patent
Yang et al.

(10) Patent No.: US 9,058,735 B2
(45) Date of Patent: Jun. 16, 2015

(54) METHOD AND SYSTEM FOR DETECTING CONDITIONS OF DRIVERS, AND ELECTRONIC APPARATUS THEREOF

(71) Applicant: Industrial Technology Research Institute, Hsinchu (TW)

(72) Inventors: Chung-Hsien Yang, Taipei (TW); Chun-Fu Chuang, Kaohsiung (TW); Syuan-Yi Chen, Changhua County (TW)

(73) Assignee: Industrial Technology Research Institute, Hsinchu (TW)

( * ) Notice: Subject to any disclaimer, the term of this patent is extended or adjusted under 35 U.S.C. 154(b) by 24 days.

(21) Appl. No.: 14/155,363

(22) Filed: Jan. 15, 2014

(65) Prior Publication Data
US 2015/0061875 A1 Mar. 5, 2015

(30) Foreign Application Priority Data

Sep. 4, 2013 (TW) .............................. 102131814 A (51) Int. Cl.
*G08B 23/00* (2006.01)
*G08B 21/02* (2006.01)
(Continued)

(52) U.S. Cl.
CPC . *G08B 21/02* (2013.01); *A61B 5/18* (2013.01); *A61B 5/1071* (2013.01); *A61B 5/1121* (2013.01); *A61B 5/6814* (2013.01)

(58) Field of Classification Search
CPC .......... G08B 21/02; G08B 21/06; A61B 5/18; A61B 5/16; A61B 5/11; A61B 5/1121; A61B 5/1122; A61B 5/1171; A61B 5/6814; B60W 2550/402; B60K 28/06

USPC .............. 340/576, 575, 573.1, 438, 439, 435, 340/425.5; 345/7–9; 180/272, 270, 269, 180/282; 280/734, 735, 736; 701/1, 301
See application file for complete search history.

(56) References Cited

U.S. PATENT DOCUMENTS

| | | | |
|---|---|---|---|
| 5,689,241 | A | 11/1997 | Clarke, Sr. et al. |
| 6,154,559 | A | 11/2000 | Beardsley |

(Continued)

FOREIGN PATENT DOCUMENTS

| CN | 2173426 | 8/1994 |
|---|---|---|
| CN | 202383802 | 8/2012 |

(Continued)

OTHER PUBLICATIONS

"Office Action of Taiwan Counterpart Application", issued on Jan. 13, 2015, p. 1-3.

(Continued)

*Primary Examiner* — Anh V La
(74) *Attorney, Agent, or Firm* — Jianq Chyun IP Office (57) ABSTRACT

A system for detecting a condition of a driver is provided, wherein the system includes a first electrical device, a second electrical device, a regulation unit and an alert unit. The first electrical device detects an initial vehicle angle of a vehicle, the second electrical device detects an initial head angle of the driver and the regulation unit calculates a regulation angle based on the initial head angle and the initial vehicle angle. Additionally, the first electrical device detects a current vehicle angle of the vehicle, the second electrical device detects a current head angle of the driver and the regulation unit calculates a regulated head angle based on the current head angle and the regulation angle. Furthermore, the alert unit calculates a difference value between the regulated head angle and the current vehicle angle and generates a warning message if the difference value is larger than a threshold.

30 Claims, 7 Drawing Sheets

(51) Int. Cl.
    *A61B 5/18*   (2006.01)
    *A61B 5/107*  (2006.01)
    *A61B 5/11*   (2006.01)
    *A61B 5/00*   (2006.01)

(56) References Cited

U.S. PATENT DOCUMENTS

| | | | |
|---|---|---|---|
| 6,717,518 B1 * | 4/2004 | Pirim et al. | 340/576 |
| 6,730,047 B2 | 5/2004 | Socci et al. | |
| 7,970,175 B2 | 6/2011 | Malawey et al. | |
| 8,340,908 B2 | 12/2012 | Hess et al. | |
| 8,344,894 B2 | 1/2013 | Szczerba et al. | |
| 8,487,775 B2 * | 7/2013 | Victor et al. | 340/576 |
| 2003/0065430 A1 | 4/2003 | Lu et al. | |
| 2010/0265074 A1 * | 10/2010 | Namba et al. | 340/576 |
| 2012/0242819 A1 | 9/2012 | Schamp | |

FOREIGN PATENT DOCUMENTS

| | | |
|---|---|---|
| EP | 1050033 | 6/2002 |
| TW | I246586 | 1/2006 |
| TW | M294713 | 7/2006 |
| TW | M353122 | 3/2009 |
| TW | M393666 | 12/2010 |
| TW | M413618 | 10/2011 |
| TW | M416161 | 11/2011 |
| TW | I395576 | 5/2013 |
| TW | 201325957 | 7/2013 |

OTHER PUBLICATIONS

Xianping Fu et al., "Automatic Calibration Method for Driver's Head Orientation in Natural Driving Environment," IEEE Transactions on Intelligent Transportation Systems, vol. 14, No. 1, Mar. 2013, pp. 303-312.

Tsuyoshi Sekitani et al., "The Design and Application of Human Attitude Detector Based on Inertial Measurement Unit," Chinese Control and Decision Conference (CCDC), May 23-25, 2011, pp. 2772-2777.

John J Sammarco and Brianna Eiter, "Measuring the Effects of Lighting Distribution on Walking Speed and Head Pitch with Wearable Inertial Measurement Units," IEEE Industry Applications Society Annual Meeting, Oct. 2012, pp. 1-7.

Satoru Fujisawa et al., "Analysis of Head Tilt Strategy of Car Drivers," ICROS-SICE International Joint Conference, Aug. 18-21, 2009 pp. 4161-4165.

Xuetao Zhang et al., "Head Pose Estimation Using Isophote Features for Driver Assistance Systems," IEEE Intelligent Vehicles Symposium, Jun. 3-5, 2009, pp. 568-572.

Henry Himberg et al., "A Multiple Model Approach to Track Head Orientation With Delta Quaternions," IEEE Transactions on Cybernetics, vol. 43, No. 1, Feb. 2013, pp. 90-101.

Jiwon J. Oh and Seibum B. Choi, "Vehicle Velocity Observer Design Using 6-D IMU and Multiple-Observer Approach," IEEE Transactions on Intelligent Transportation Systems, vol. 13, No. 4, Dec. 2012, pp. 1865-1879.

* cited by examiner

METHOD AND SYSTEM FOR DETECTING CONDITIONS OF DRIVERS, AND ELECTRONIC APPARATUS THEREOF

CROSS-REFERENCE TO RELATED APPLICATION

This application claims the priority benefit of Taiwan application serial no. 102131814, filed on Sep. 4, 2013. The entirety of the above-mentioned patent application is hereby incorporated by reference herein and made a part of this specification.

BACKGROUND

1. Technical Field

The present disclosure relates to a method for detecting conditions of drivers, a system for detecting conditions of drivers, and electronic apparatus using the system.

2. Related Art

In recent years, along with the development of the vehicle technology, the vehicles are used popularly in the whole world. Although it brought the convenience of life for mankind, the casualties caused by traffic accident are still high. Therefore, developed countries and major depots are actively seeking how to apply science and technology on the vehicle, in order to improve vehicle safety and reduce accident rates. An occurrence of a traffic accident often results largely from human factors. For example, fatigue and distraction are often the main cause of the accident. The above-mentioned distracted driving behaviour may be identified by observing a head posture of a driver.

Additionally, along with the development of the electronic technology, the size of electronic components is unceasingly reduces, and power consumption is also decreased. For example, Google Glass or Smart Watch has been leading the next generation of wearable technology. In addition, many companies, such as Amazon, Facebook, NIKE, Microsoft and so on, have invested in the related technologies research and development, e.g., smart clothing, telephone gloves, fitness jogging shoes, the healthy wrist belt and the intelligent sock, etc. Therefore, the growth of wearable technology should not be underestimated.

SUMMARY

Accordingly, the present disclosure is related to a method for detecting conditions of drivers, a system for detecting conditions of drivers, and electronic apparatus using the system, which are capable of detecting the status of the vehicle and the driver, and issuing a warning message to remind the driver when distracted driving or abnormal phenomenon occurs, thereby achieving the traffic safety.

In an exemplary embodiment of the disclosure, a system for detecting conditions of drivers is provided. The system comprises a first electrical device, a second electrical device, a regulation unit and an alert unit. The first electrical device includes a first sensor coupling to a first communication unit, wherein the first sensor is configured to detect an initial vehicle angle of a vehicle on a first dimension. The second electrical device includes a second sensor coupling to a second communication unit, wherein the second sensor is configured to detect an initial head angle of the driver on the first dimension. The regulation unit is disposed in the first electrical device or the second electrical device to calculate a regulation angle on the first dimension based the initial vehicle angle and the initial head angle on the first dimension. The alert unit is disposed in the first electrical device or the second electrical device. The first sensor detects a current vehicle angle of the vehicle on the first dimension, and the second sensor detects a current head angle of the driver on the first dimension. The regulation unit calculates a regulated head angle of the driver on the first dimension based on the current head angle and the regulation angle on the first dimension. The alert unit calculates a difference value between the current vehicle angle and the regulated head angle on the first dimension and determines whether the absolute value of the difference value is larger than a first threshold. If the absolute value of the difference value is larger than the first threshold, the alert unit generates a warning message.

In an exemplary embodiment of the disclosure, an electronic apparatus is provided. The electronic apparatus comprises a micro-controller, a sensor, a communication unit, a regulation unit and an alert unit. The sensor is coupled to the micro-controller and configured to detect an initial angle and a current angle of the electronic apparatus on first dimension. The communication unit is coupled to the micro-controller and configured to receive a first signal of an initial angle of another electronic apparatus on the first dimension, and receive a second signal of a current angle of the another electronic apparatus on the first dimension. The regulation unit is coupled to the micro-controller, and the regulation unit calculates a regulation angle on first dimension based on the initial angle of the electronic apparatus and the initial angle of the another electronic apparatus on the first dimension, and calculates a regulated angle on the first dimension based on the regulation angle on the first dimension to adjust one of the current angle of the electronic apparatus and the current angle of the another electronic apparatus on the first dimension. The alert unit is coupled to the micro-controller, and the alert unit calculates a difference value between one of the current angle of the electronic apparatus and the another electronic apparatus and the regulated angle on the first dimension. The alert unit determines whether the absolute value of the difference value is larger than a first threshold. If the absolute value of the difference value is larger than the first threshold, the alert unit generates a warning message.

In an exemplary embodiment of the disclosure, a method for detecting a condition of a driver is provided. The method includes following steps. An initial vehicle angle of a vehicle on a first dimension and an initial head angle of the driver on the first dimension are detected. A regulation signal is read to determine whether to perform a regulation process, and when the regulation signal is read, and a regulation angle on the first dimension is calculated based on the initial head angle and the initial vehicle angle on the first dimension. A current vehicle angle of the vehicle on the first dimension and a current head angle of the driver on the first dimension are detected. A regulated head angle on the first dimension is calculated based on the current head angle and the regulation angle on the first dimension. A difference value is calculated between the current vehicle angle and the regulated head angle on the first dimension. Whether the absolute value of the difference value is larger than a first threshold is determined and if the absolute value of the difference value is larger than the first threshold, a warning message is generated.

In another exemplary embodiment of the disclosure, a system for detecting conditions of drivers is provided. The system comprises a first electrical device, a second electrical device, a regulation unit and an alert unit. The first electrical device includes a first sensor coupling to a first communication unit, wherein the first sensor is configured to detect an initial vehicle angular velocity of a vehicle on a first dimension. The second electrical device includes a second sensor coupling to a second communication unit, wherein the second sensor is configured to detect an initial head angular velocity of the driver on the first dimension. The regulation unit is disposed in the first electrical device or the second electrical device to calculate a regulation angular velocity on the first dimension based on the initial vehicle angular velocity and the initial head angular velocity on the first dimension. The alert unit is disposed in the first electrical device or the second electrical device. The first sensor detects a current vehicle angular velocity of the vehicle on the first dimension, and the second sensor detects a current head angular velocity of the driver on the first dimension. The regulation unit calculates a regulated head angular velocity of the driver on the first dimension based on the current head angular velocity and the regulation angular velocity on the first dimension. The alert unit calculates an angular velocity difference value between the current vehicle angular velocity and the regulated head angular velocity on the first dimension and determines whether the absolute value of the angular velocity difference value is larger than a first threshold. If the absolute value of the angular velocity difference value is larger than the first threshold, the alert unit generates a warning message.

In another exemplary embodiment of the disclosure, an electronic apparatus is provided. The electronic apparatus comprises a micro-controller, a sensor, a communication unit, a regulation unit and an alert unit. The sensor is coupled to the micro-controller and configured to detect an initial angular velocity and a current angular velocity of the electronic apparatus on a first dimension of. The communication unit is coupled to the micro-controller and configured to receive a first signal of an initial angular velocity of another electronic apparatus on the first dimension, and receive a second signal of a current angular velocity of the another electronic apparatus on the first dimension. The regulation unit is coupled to the micro-controller, and the regulation unit calculates a regulation angular velocity on the first dimension based on the initial angular velocity of the electronic apparatus and the initial angular velocity of the another electronic apparatus on the first dimension, and calculates a regulated angular velocity on the first dimension based on the first dimension of the regulation angular velocity to adjust one of the current angular velocity of the electronic apparatus on the first dimension and the current angular velocity of the another electronic apparatus on the first dimension. The alert unit is coupled to the micro-controller, and the alert unit calculates the absolute value of an angular velocity difference value between one of the current angular velocity of the electronic apparatus and the another electronic apparatus on the first dimension and the regulated angular velocity on the first dimension. The alert unit determines whether the absolute value of the angular velocity difference value is larger than a first threshold. If the absolute value of the angular velocity difference value is larger than the first threshold, the alert unit generates a warning message.

In an exemplary embodiment of the disclosure, a method for detecting a condition of a driver is provided. The method includes following steps. An initial vehicle angular velocity of a vehicle on a first dimension and an initial head angular velocity of the driver on the first dimension are detected. A regulation signal is read to determine whether to perform a regulation process, and when the regulation signal is read, calculating a regulation angular velocity on the first dimension is calculated based on the initial head angular velocity and the initial vehicle angular velocity on the first dimension. A current vehicle angular velocity of the vehicle on the first dimension and a current head angular velocity of the driver on the first dimension are detected. A regulated head angular velocity on the first dimension is calculated based on the current head angular velocity on the first dimension and the regulation angular velocity on the first dimension. An angular velocity difference value is calculated between the current vehicle angular velocity and the regulated head angular velocity on the first dimension. Whether the absolute value of the first dimension of the angular velocity difference value is larger than a first threshold is determined, and if the absolute value of the first dimension of the angular velocity difference value is larger than the first threshold, a warning message is generated.

In order to make the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DETAILED DESCRIPTION OF DISCLOSED EMBODIMENTS

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
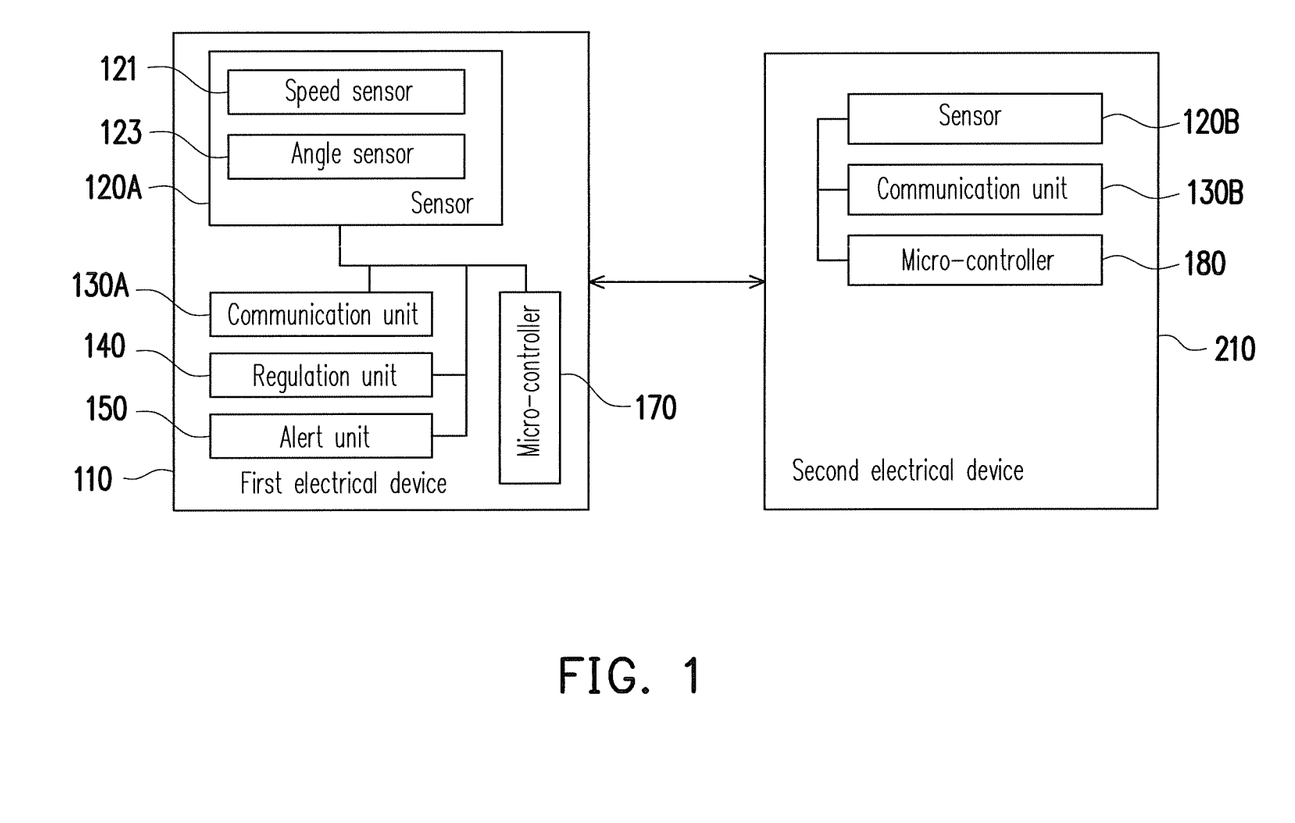
FIG. 1 is a block diagram of a system for detecting conditions of drivers according to an exemplary embodiment of the disclosure.

FIG. 1 is a block diagram of a system for detecting conditions of drivers according to an exemplary embodiment of the disclosure, which is only used as an example, and is not used to limit the present disclosure.

Referring to FIG. 1, the system for detecting conditions of drivers includes a first electrical device 110, a second electrical device 210, a regulation unit 140 and an alert unit 150. The first electrical device 110 is used for a vehicle and includes a micro-controller 170, a sensor 120A and a communication unit 130A. The micro-controller 170 is configured to control the overall operation of the first electrical device 110. The sensor 120A and the communication unit 130A are coupled to the micro-controller 170, wherein the sensor 120A is configured to detect an initial vehicle angle of the vehicle on a first dimension, and the communication unit 130A is configured to communicate with another electrical device.

The second electrical device 210 is used for a user terminal (for example, a driver side). The second electrical device 210 includes a micro-controller 180, a sensor 120B and a communication unit 130B. The micro-controller 180 is configured to control the overall operation of the second electrical device 210. The sensor 120B and the communication unit 130B are coupled to the micro-controller 180, wherein the sensor 120B is configured to detect an initial head angle of the driver on the first dimension, and the communication unit 130B is configured to communicate with another electrical device.

In the present exemplary embodiment, each of the sensor 120A of the first electrical device 110 and the sensor 120B of the second electrical device 210 may be an electronic compass or a magnetometer used for measuring the absolute angle. For example, when the first electrical device 110 is disposed in the vehicle, the sensor 120A may detect the absolute angle of the vehicle. When the second electrical device 210 is disposed in the wear material (e.g., glasses, hat) worn on the head of the driver, the sensor 120B may detect the absolute angle of the driver's head.

In the present exemplary embodiment, each of the communication unit 130A of the first electrical device 110 and the communication unit 130B of the second electrical device 210 may be wireless communication unit or wired communication unit.

The regulation unit 140 is disposed in the first electrical device 110, and the regulation unit 140 calculates a regulation angle on the first dimension based on the initial head angle and the initial vehicle angle on the first dimension. Specifically, the second electrical device 210 transmits the initial head angle on the first dimension via the communication unit 130B to the communication unit 130A of the first electrical device 110. The communication unit 130A of the first electrical device 110 receives the initial head angle on the first dimension, the sensor 120A detects the initial vehicle angle on the first dimension, and the regulation unit 140 calculates the regulation angle on the first dimension. Although in the present exemplary embodiment, the regulation unit 140 is disposed in the first electrical device 110, but the present disclosure is not limited thereto. For example, in another exemplary embodiment, the regulation unit 140 may be disposed in the second electrical device 210.

The alert unit 150 is disposed in the first electrical device 110, and the alert unit 150 determines whether to issue a warning message according to a difference value between the angle detecting by the sensor 120A and the angle detecting by the sensor 120B.

Specifically, the sensor 120A may continue to detect a current vehicle angle of the vehicle on the first dimension, and the sensor 120B may continue to detect a current head angle of the driver on the first dimension. The communication unit 130B of the second electrical device 210 may continue to transmit the current head angle detected by the sensor 120B on the first dimension to the communication unit 130A of the first electrical device 110. In addition, the regulation unit 140 calculates a regulated head angle on the first dimension based on the current head angle and the regulation angle on the first dimension. For example, the regulated head angle on the first dimension may be obtained by subtracting the regulation angle from the current head angle on the first dimension. In particular, the alert unit 150 calculates a difference value between the current vehicle angle and the regulated head angle on the first dimension and determines whether the absolute value of the difference value is larger than a first threshold. If the absolute value of the difference value is larger than the first threshold, the alert unit 150 generates a warning message.

In the present exemplary embodiment, for example, the alert unit 150 issues the warning message by playing a sound. However, the disclosure is not limited thereto. In another exemplary embodiment, the alert unit 150 may also play video, generate vibration or use a combination of at least two of voice, video and vibration to generate the warning message.

In another exemplary embodiment, the alert unit 150 calculates a predetermined time. And, the alert unit 150 generates the warning message when the absolute value of the difference value is larger than the first threshold and continues the predetermined time, thereby avoiding a misjudgment.

In the present exemplary embodiment, the alert unit 150 is disposed in the first electrical device 110, but the present disclosure is not limited thereto. For example, in another exemplary embodiment, the alert unit 150 may be disposed in the second electrical device 210. Furthermore, in another exemplary embodiment, the alert unit 150 may be a separate device, and receives information about the absolute angle transmitted from the first electrical device 110 or the second electrical device 210 through the communication interface.

In the present exemplary embodiment, the sensor 120A detects a current vehicle speed of the vehicle. The alert unit 150 determines whether the current vehicle speed is larger than a vehicle speed threshold. Here, the alert unit 150 generates the warning message when the absolute value of the difference value is larger than the first threshold and the current vehicle speed is larger than the vehicle speed threshold.

In detail, the sensor 120A of the first electrical device 110 includes a speed sensor 121 and an angle sensor 123. The speed sensor 121 detects the current vehicle speed. The angle sensor 123 detects the initial vehicle angle and the current vehicle angle on the first dimension.

In another exemplary embodiment, the regulation unit 140 may be disposed in the second electrical device 210. When the regulation unit 140 is disposed in the second electrical device 210, the communication unit 130A of the first electrical device 110 transmits the initial vehicle angle and the current vehicle angle on the first dimension to the second electrical device 210. The regulation unit 140 calculates the regulation angle on the first dimension based on the initial vehicle angle and the initial head angle detected by the sensor 120B of the second electrical device 210 on the first dimension. Then, the regulation unit 140 calculates the regulated head angle on the first dimension based on the current head angle and the regulation angle on the first dimension. When the regulation unit 140 is disposed in the second electrical device 210, the first electrical device 110 may not disposed with the regulation unit 140.

In another exemplary embodiment, the communication unit 130A of the first electrical device 110 and the communication unit 130B of the second electrical device 210 may be connected with a remote server (not shown) and transmit the vehicle speed, the vehicle angle, the head angle or the regulated head angle to the remote server. For example, the remote server of the logistics and distribution industry, passenger transport operators or insurers may monitor the vehicles and the drivers in real-time. And, the first electrical device 110 and the second electrical device 210 may receive the information sent by the remote server, such as threshold settings information. In particular, in the present exemplary embodiment, the alert unit 150 transmits the warning message to the remote server through the communication units 130A and 130B.

Although in the above exemplary embodiment, the first electrical device 110 and the second electrical device 210 detect the vehicle angles and the driver's head angles on the first dimension to determine whether to issue the warning message. However, the present disclosure is not limited thereto. The system and method of the present exemplary embodiment may determine whether to issue a warning message according to the vehicle angles and driver's head angles on multiple dimensions.

For example, the sensor 120A further detects an initial vehicle angle of the vehicle on a second dimension, and the sensor 120B detects an initial head angle of the driver on the second dimension. The regulation unit 140 calculates a regulation angle on the second dimension based on the initial vehicle angle and the initial head angle on the second dimension. The sensor 120A may continue to detect a current vehicle angle of the vehicle on the second dimension, and the sensor 120B may continue to detect a current head angle of the driver on the second dimension, and the regulation unit 140 calculates a regulated head angle on the second dimension based on the current head angle and the regulation angle on the second dimension. The alert unit 150 calculates a difference value between the current vehicle angle and the regulated head angle on the second dimension and determines whether the absolute value of the difference value is larger than a second threshold. If the absolute value of the difference value is larger than the second threshold, the alert unit 150 generates a warning message.

As another example, the sensor 120A further detects an initial vehicle angle of the vehicle on a third dimension, and the sensor 120B detects an initial head angle of the driver on the third dimension. The regulation unit 140 calculates a regulation angle on the third dimension based on the initial vehicle angle and the initial head angle on the third dimension. The sensor 120A may continue to detect a current vehicle angle of the vehicle on the third dimension, and the sensor 120B may continue to detect a current head angle of the driver on the third dimension, and the regulation unit 140 calculates a regulated head angle on the third dimension based on the current head angle and the third dimension of the regulation angle on the third dimension. The alert unit 150 calculates a difference value between the current vehicle angle and the regulated head angle on the third dimension and determines whether the absolute value of the difference value is larger than a third threshold. If the absolute value of the difference value is larger than the third threshold, then the alert unit 150 generates a warning message.

In the present exemplary embodiment, the sensor 120A of the first electrical device 110 and the sensor 120B of the second electrical device 210 may be 3-axis electronic compasses used to measure the absolute angle of the vehicle and the driver. For example, each of the sensors 120A and 120B detects the yaw angle, the pitch angle and the roll angle. The above-mentioned the first dimension, the second dimension and the third dimension may be one of the yaw angle, the pitch angle and the roll angle respectively. Therefore, the absolute value of the difference value $\Delta\theta_{Yaw,Roll,Pitch}^{P,car}$ between the current vehicle angle and the regulated head angle may be at least one of the three dimensions of the absolute value of the yaw angle $\Delta\theta_{Yaw}^{P,car}$, the absolute value of the pitch angle $\Delta\theta_{Pitch}^{P,car}$ and the absolute value of the roll angle $\Delta\theta_{Roll}^{P,car}$, respectively.

In another exemplary embodiment, after obtaining the absolute angle, the angular velocity $\omega$ may be calculated through the relationship between the angles and time (i.e., the rate of change of angles). The angular velocity $\omega$ includes the yaw angular velocity, the pitch angular velocity and the roll angular velocity. Similarly, the regulation angular velocity may be calculated based on the regulation angle, and the regulation angular velocity includes the regulation yaw angular velocity, the regulation pitch angular velocity and the regulation roll angular velocity. And, the absolute value of the angular velocity difference value $\Delta\omega_{Yaw,Roll,Pitch}^{P,car}$ may be calculated based on the absolute value of the difference value $\Delta\theta_{Yaw,Roll,Pitch}^{P,car}$. The absolute value of the angular velocity difference value may be at least one of the absolute value of the yaw angular velocity $\Delta\omega_{Yaw}^{P,car}$, the pitch angular velocity $\Delta\omega_{Pitch}^{P,car}$, the roll angular velocity $\Delta\omega_{Roll}^{P,car}$, or a combination thereof.

In the present exemplary embodiment, the first electrical device 110 may be disposed in the vehicle or be a portable terminal device. The portable terminal device may be attached to the vehicle or separated with the vehicle, such as a smart phone, a tablet PCs, a GPS (global positioning system) navigation device, an EDR (event data recorder), an OBD (on-board diagnostics) and so on.

The second electrical device 210 is used for detecting the position and the status of the driver. In particular, in the present exemplary embodiment, the second electrical device 210 detects the head posture of the driver to determine whether the driver is distractedly driving. The second electrical device 210 may be a wearable electrical device, such as glasses, a hat, a head band, or an electrical device attachable to the driver's hat.

It should be noticed that in the present exemplary embodiment, the regulation unit 140 and the alert unit 150 are implemented in hardware, but the present disclosure is not limited thereto. For example, the regulation unit 140 and the alert unit 150 may also be implemented in software or firmware codes, and stored in the storage circuit of the first electronic device 110 or the second electronic device 210. When the first electronic device 110 or the second electronic device 210 is activated, the software or firmware codes implementing the regulation unit 140 and the alert unit 150 may be executed on the micro-controller to perform the method for detecting conditions of drivers of the disclosure.

Figure 2:
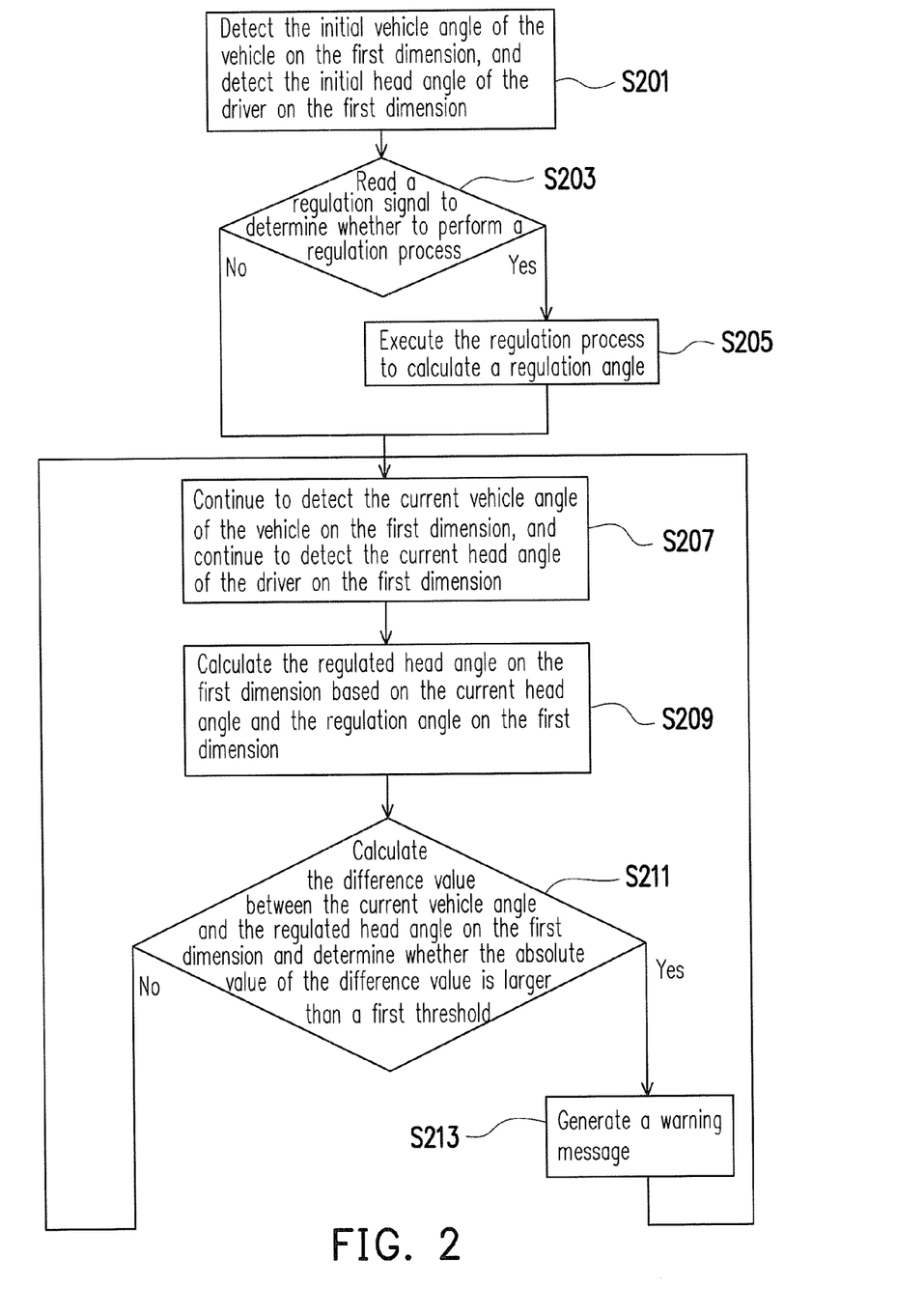
FIG. 2 is a flowchart illustrating a method for detecting conditions of drivers according to an exemplary embodiment of the disclosure.

FIG. 2 is a flowchart illustrating a method for detecting conditions of drivers according to an exemplary embodiment of the disclosure.

Referring to FIG. 1 and FIG. 2, first, the first electrical device 110 detects the initial vehicle angle of the vehicle on the first dimension, and the second electrical device 210 detects the initial head angle of the driver on the first dimension (step S201).

The regulation unit 140 reads a regulation signal to determine whether to perform a regulation process (step S203). In the present exemplary embodiment, when the first electrical device 110 or the second electrical device 210 is activated, the first electrical device 110 or the second electrical device 210 automatically send the regulation signal to perform the regulation process. In another exemplary embodiment, the first electrical device 110 or the second electrical device 210 may be equipped with a regulation switch (not shown), and the driver manually activates the regulation switch to perform the regulation process. For example, if the second electrical device 210 disposed on the driver's head is moved or skewed, the driver may manually activate the regulation switch to perform the regulation process again.

When reading the regulation signal, the regulation process will be executed (step S205). Specifically, the regulation process calculates the regulation angle on the first dimension based on the initial head angle and the initial vehicle angle on the first dimension. On the contrary, if no regulation signal is read, it means that the first electrical device 110 or the second electrical device 210 had been performed the regulation process. And the first electrical device 110 continues to detect the current vehicle angle of the vehicle on the first dimension, and the second electrical device 210 continues to detect the current head angle of the driver on the first dimension (step S207). Then, the regulation unit 140 calculates the regulated head angle on the first dimension based on the current head angle and the regulation angle on the first dimension (step S209). The alert unit 150 calculates the difference value between the current vehicle angle and the regulated head angle on the first dimension and determines whether the absolute value of the difference value is larger than a first threshold (step S211). If the absolute value of the difference value is larger than the first threshold, the alert unit 150 generates a warning message (step S213).

In the present exemplary embodiment, the method for detecting conditions of drivers may further comprise detecting the current vehicle speed of the vehicle, and determines whether the current vehicle speed is larger than the vehicle speed threshold. If the current vehicle speed doesn't exceed the vehicle speed threshold (for example, 5 Km/h), it means the vehicle speed is too slow or still, then keeps detecting the current vehicle speed and doesn't execute subsequent processes. If the current vehicle speed exceeds the vehicle speed threshold, the steps of detecting distracted driving will be executed. That is, when the absolute value of the difference value is larger than the first threshold and the current vehicle speed is larger than the vehicle speed threshold, the step of generating the warning message is executed.

In the above-mentioned steps of exemplary embodiment, the first electrical device 110 or the second electrical device 210 detects the initial vehicle angle, the initial head angle, the regulation angle, the current vehicle angle, the current head angle, the regulated head angle and the difference value on the first dimension, but the present disclosure is not limited thereto. In another exemplary embodiment, the first electrical device 110 or the second electrical device 210 may also detect the initial vehicle angle, the initial head angle, the regulation angle, the current vehicle angle, the current head angle, the regulated head angle and the difference value on the second dimension or the third dimension. If the absolute value of the difference value on the second dimension is larger than the second threshold, a warning message is generated. Or if the absolute value of the difference value on the third dimension is larger than the third threshold, a warning message is generated. The above-mentioned the first dimension, the second dimension and the third dimension may be one of the yaw angle, the pitch angle and the roll angle, respectively.

The above-mentioned step S203 (i.e., the step of determining whether to perform the regulation process), step S205 (i.e., the regulation process), steps S209, S211 (i.e., the step of detecting distracted driving) and step S213 (i.e., the step of generating the warning message) may be executed on the first electrical device 110 or the second electrical device 210.

In step S211, in addition to identifying the distracted driving based on the absolute value of the difference value $|\Delta\theta_{Yaw,Row,Pitch}^{P,car}|$ on the first dimension, which is larger than the first threshold, a predetermined time further is calculated and considered to determine whether the user is distractedly driving. In one exemplary embodiment, when the absolute value of the difference value on the first dimension continuously is larger than the first threshold for the predetermined time, the step of generating a warning message is executed. For example, when the absolute value of the difference value on the first dimension is larger than the first threshold θ (i.e., 5°) for 3 seconds, the warning message is issued.

In another exemplary embodiment, the angular velocity ω is calculated based on the rate of change of angles and time. Therefore, the flowchart in FIG. 2, the angles in step S201 to step S211 may be replaced with the angular velocity ω, so that the vehicle angular velocities are calculated based on the vehicle angles, the head angular velocities are calculated based on the head angles, the absolute value of the angular velocity difference value $\Delta\omega_{Yaw,Roll,Pitch}^{P,car}$ is calculated based on the absolute value of the difference value $\Delta\theta_{Yaw,Roll,Pitch}^{P,car}$. Accordingly, in step S211, whether the absolute value of the angular velocity difference value on the first dimension is larger than the first threshold is determined, wherein the first threshold may be added with the driving oscillating frequency parameter for detecting distracted driving. For example, when the absolute value of the angular velocity difference value is larger than the threshold Δω and the wavering frequency of a driver reaches an oscillating frequency parameter f, it means distracted driving, i.e., the driver's head swings regularly (probably doze off), the posture of the driver's head is maintained for a long time (e.g., watching a view outside the window or talking with the passenger), the driver picks up something or operates a cell phone. Accordingly, the alert unit 151) issues the warning message.

Next, the calculating of the regulation angular velocity, the executing of the regulation process, and the calculating of the difference value between the current vehicle angle and the regulated head angle according to the present exemplary embodiment are describe hereinafter.

Figure 3A:
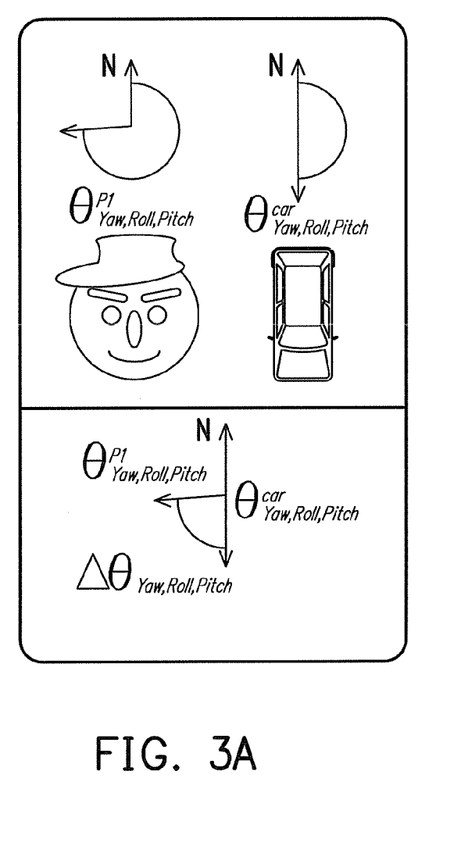
FIGS. 3A~3B are schematic diagrams illustrating a regulation process according to an exemplary embodiment of the disclosure.
Figure 3B:
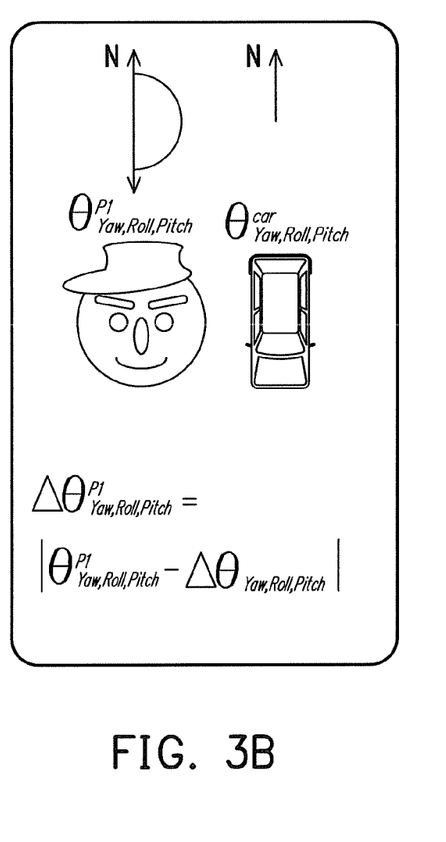

FIGS. 3A~3B are schematic diagrams illustrating a regulation process according to an exemplary embodiment of the disclosure.

In the present exemplary embodiment, the second electrical device 210 is disposed in the driver's hat. Referring to FIG. 3A, first, the first electrical device 110 detects the initial vehicle angle $\theta_{Yaw,Roll,Pitch}^{car}$ of the vehicle. In addition, the driver is facing the front of the vehicle, and the second electrical device 210 of the driver's hat detects the initial head angle $\theta_{Yaw,Roll,Pitch}^{P1}$ of the driver. So the regulation unit 140 calculates the absolute value of the regulation angle $\Delta\theta_{Yaw,Roll,Pitch}$ based on the initial head angle and the initial vehicle angle (i.e. $\Delta\theta_{Yaw,Roll,Pitch}=|\theta_{Yaw,Roll,Pitch}^{P}-\theta_{Yaw,Roll,Pitch}^{car}|$). If the regulation angle $\Delta\theta_{Yaw,Roll,Pitch}$ is 0°, then there is no deviation between the angles of the first electronic device 110 and the second electronic device 210 or the regulation unit 140 has been performed the regulation process. In the present exemplary embodiment, the initial vehicle angle $\theta_{Yaw,Roll,Pitch}^{car}$ is at least one of the three dimensions of the absolute vehicle yaw angle $\theta_{Yaw}^{car}$, the absolute vehicle pitch angle $\theta_{Pitch}^{car}$, the absolute vehicle roll angle $\theta_{Roll}^{car}$ or a combination thereof. The initial head angle $\theta_{Yaw,Roll,Pitch}^{P1}$ is at least one of the three dimensions of the absolute driver yaw angle $\theta_{Yaw}^{car}$, the absolute driver pitch angle $\theta_{Pitch}^{car}$ the absolute driver roll angle $\theta_{Roll}^{car}$ or a combination thereof. In the present exemplary embodiment, the initial vehicle angle $\theta_{Yaw,Roll,Pitch}^{car}$ is 180°, the initial head angle $\theta_{Yaw,Roll,Pitch}^{P1}$ is 225°, then the regulation angle $\Delta\theta_{Yaw,Roll,Pitch}$ is 45° (i.e., |225°−180°|=45°).

Referring to FIG. 3B, an initial regulated head angle $\Delta\theta_{Yaw,Roll,Pitch}^{P1}$ is equal to the absolute value obtained by subtracting the regulation angle $\Delta\theta_{Yaw,Roll,Pitch}$ from the initial head angle $\theta_{Yaw,Roll,Pitch}^{P1}$ (i.e., $\Delta\theta_{Yaw,Roll,Pitch}^{P1}=|\theta_{Yaw,Roll,Pitch}^{P1}-\Delta\theta_{Yaw,Roll,Pitch}|$). The initial regulated head angle $\Delta\theta_{Yaw,Roll,Pitch}^{P1}$ is 180° (i.e., |225°−45°|=180°). Then the initial regulated head angle $\Delta\theta_{Yaw,Roll,Pitch}^{P1}$ is equal to the initial vehicle angle $\theta_{Yaw,Roll,Pitch}^{car}$ (i.e., 180°, thereby completing the regulation process.

Figure 3C:
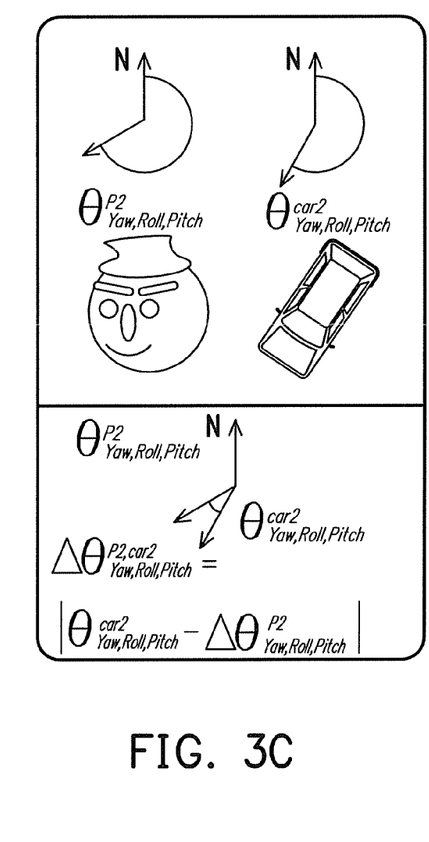
FIG. 3C is a schematic diagram illustrating an example of calculating a difference value according to an exemplary embodiment of the disclosure.

FIG. 3C is a schematic diagram illustrating an example of calculating a difference value according to an exemplary embodiment of the disclosure.

Referring to FIG. 3A, FIG. 3B and FIG. 3C, the first electrical device 110 and the second electrical device 210 continue to detect the current vehicle angle $\theta_{Yaw,Roll,Pitch}^{car2}$ and the current head angle $\theta_{Yaw,Roll,Pitch}^{P2}$, and the regulation angle $\Delta\theta_{Yaw,Roll,Pitch}$ is obtained from FIG. 3A and the regulated head angle $\Delta\theta_{Yaw,Roll,Pitch}^{P2}$ is obtained from FIG. 3B. How to calculate the difference value $\Delta\theta_{Yaw,Roll,Pitch}^{P2,car2}$ between the current vehicle angle $\theta_{Yaw,Roll,Pitch}^{car2}$ and the regulated head angle $\Delta\theta_{Yaw,Roll,Pitch}^{P2}$ is described in FIG. 3C.

Referring to FIG. 3C, the difference value $\Delta\theta_{Yaw,Roll,Pitch}^{P2,car2}$ equal to the absolute value obtained by subtracting the regulated head angle $\Delta\theta_{Yaw,Roll,Pitch}^{P2}$ from the current vehicle angle $\theta_{Yaw,Roll,Pitch}^{car2}$ (i.e., $\Delta\theta_{Yaw,Roll,Pitch}^{P2,car2}=|\theta_{Yaw,Roll,Pitch}^{car2}-\Delta\theta_{Yaw,Roll,Pitch}^{P2}|$). In the present exemplary embodiment, the current vehicle angle $\theta_{Yaw,Roll,Pitch}^{car2}$ is 180°, the current head angle $\theta_{Yaw,Roll,Pitch}^{P2}$ is 220°, and the regulation angle $\Delta\theta_{Yaw,Roll,Pitch}$ is 45°. Then the absolute value of the regulated head angle $\Delta\theta_{Yaw,Roll,Pitch}^{P2}$ is 175° (i.e., $\Delta\theta_{Yaw,Roll,Pitch}^{P2}=|\theta_{Yaw,Roll,Pitch}^{P2}-\Delta\theta_{Yaw,Roll,Pitch}|=|220°-45°|=175°$, and the absolute value of the difference value $\Delta\theta_{Yaw,Roll,Pitch}^{P2,car2}$ is 15° (i.e., $\Delta\theta_{Yaw,Roll,Pitch}^{P2,car2}=|\theta_{Yaw,Roll,Pitch}^{car2}-\Delta\theta_{Yaw,Roll,Pitch}^{P2}|=|190°-175°|=15°$). So the current head angle is not parallel with the current vehicle angle according to the absolute value of the difference value $\Delta\theta_{Yaw,Roll,Pitch}^{P2,car2}$, it means the driver is not facing the front. In particular, when the threshold of the difference value is set to 5°, so in the present exemplary embodiment, the absolute value of the difference value $\Delta\theta_{Yaw,Roll,Pitch}^{P2,car2}=15°$ is larger than the threshold (5°), then alert unit issues a warning message.

Figure 4A:
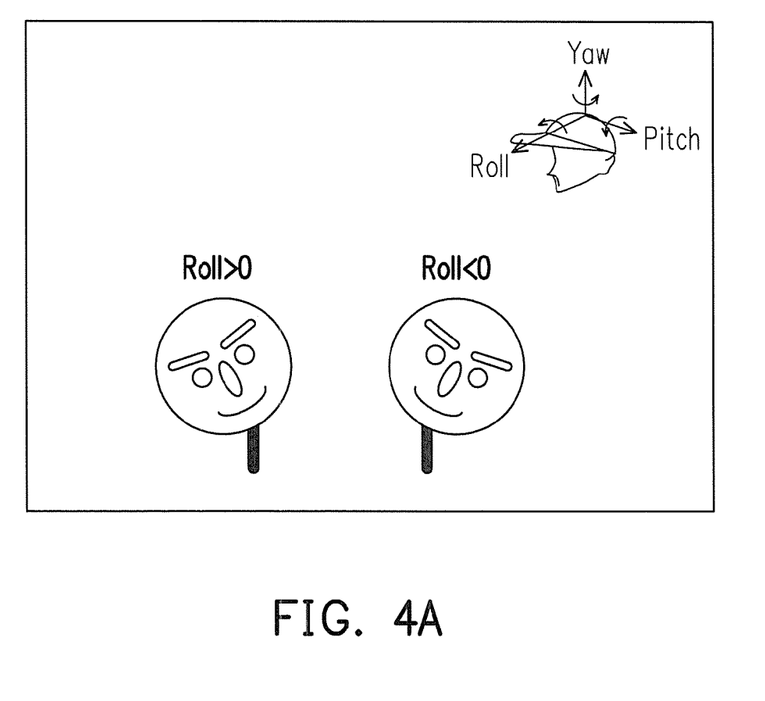
FIGS. 4A~4C are schematic diagrams illustrating an example of detecting distracted driving according to an exemplary embodiment.
Figure 4B:
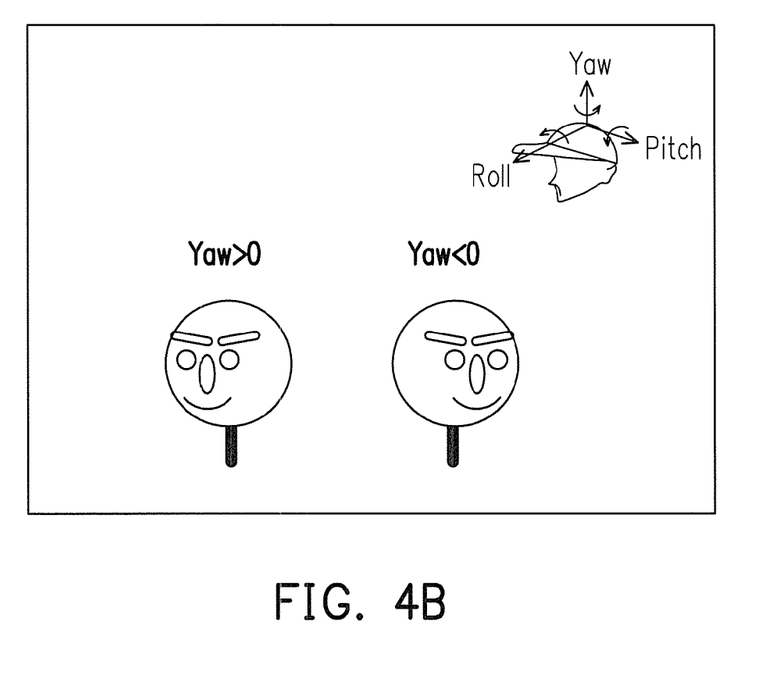
Figure 4C:
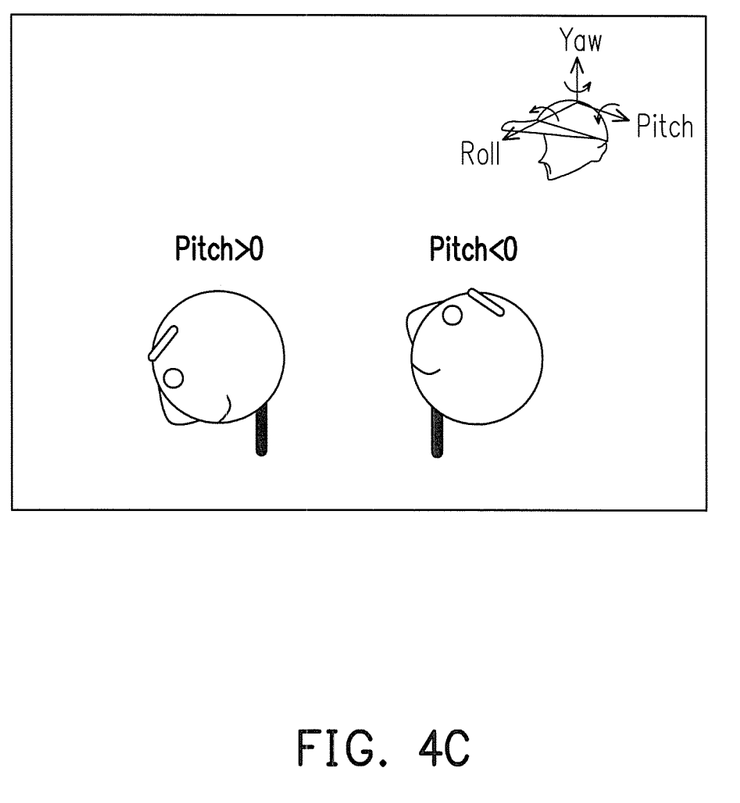

FIGS. 4A~4C are schematic diagrams illustrating an example of detecting distracted driving according to an exemplary embodiment.

Referring to FIG. 4A~4C, in the present exemplary embodiment, the detection of distracted driving depends on the relationship between the head angle of the driver and the time. For example, the driver watches a view outside the window view for a long time or bows to pick up something, etc.

FIG. 4A is the schematic diagram illustrating the absolute value of the difference value of the roll angle $\Delta\theta_{Roll}^{P,car}$ is larger than the threshold $\theta_R$ for a predetermined time Ts. FIG. 4B is the schematic diagram illustrating the absolute value of the difference value of the yaw angle $\Delta\theta_{Yaw}^{P,car}$ is larger than the threshold $\theta_Y$ for the predetermined time Ts. FIG. 4C is the schematic diagram illustrating the absolute value of the difference value of the pitch angle $\Delta\theta_{Pitch}^{P,car}$ is larger than the threshold $\theta_P$ for the predetermined time Ts. As long as the relationship between the head angle of the driver and the time in FIG. 4A~4C meet at least one of cases, it is determined that distracted driving, and the message is issued to alert the driver to concentrate.

Figure 5A:
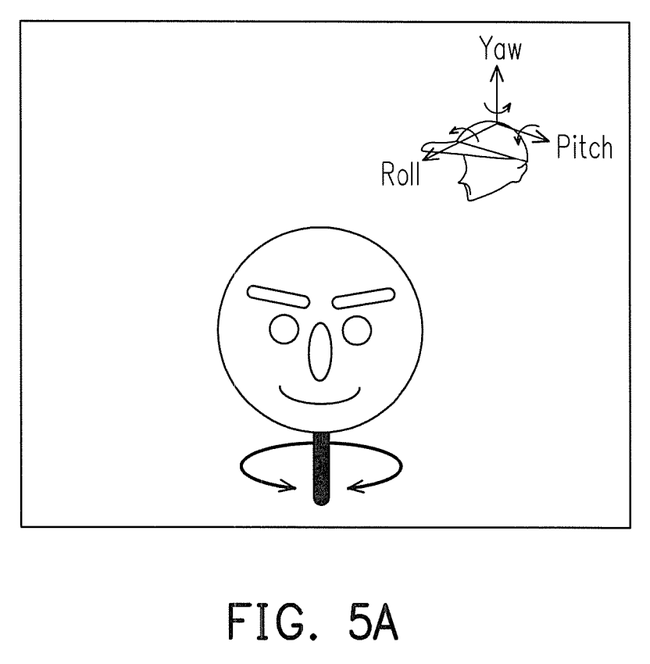
FIGS. 5A~5C are schematic diagrams illustrating an example of detecting distracted driving according to another exemplary embodiment.
Figure 5B:
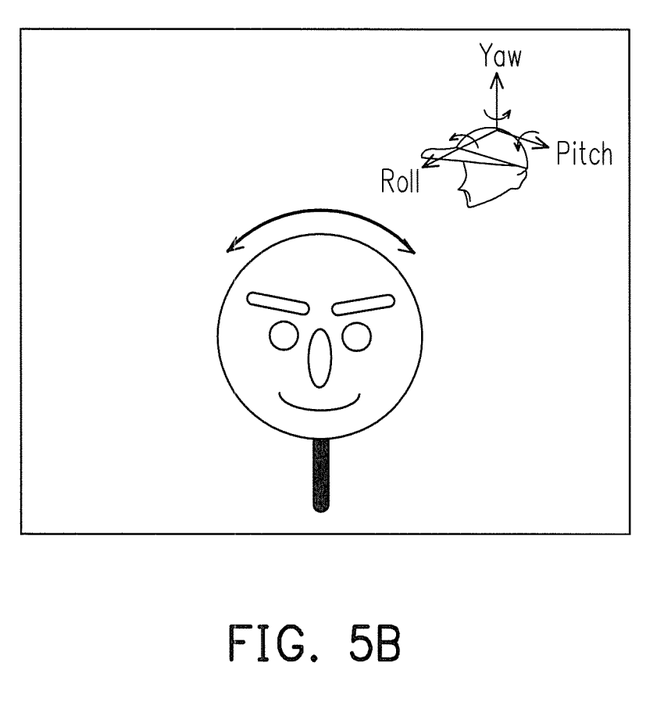
Figure 5C:
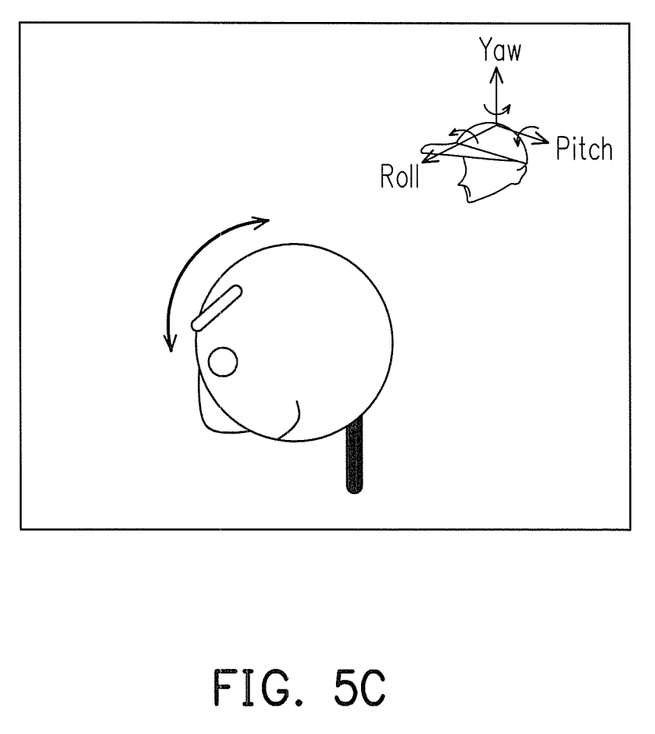

FIGS. 5A~5C are schematic diagrams illustrating an example of detecting distracted driving according to another exemplary embodiment.

Referring to FIG. 5A~5C, in the present exemplary embodiment, the detection distracted driving depends on the relationship between the angular velocity of the driver and the frequency. For example, the driver's head swings (i.e., dozing off) or the drive turns to talk with passengers, etc.

FIG. 5A is the schematic diagram illustrating the absolute value of the angular velocity difference value of the roll angle $\Delta\omega_{Roll}^{P,car}$ is larger than the threshold $\omega_R$ and exceeds a certain frequency f. FIG. 5B is the schematic diagram illustrating the absolute value of the angular velocity difference value of the yaw angle $\Delta\omega_{Yaw}^{P,car}$ is larger than the threshold $\omega_Y$ and exceeds a certain frequency f. FIG. 5C is the schematic diagram illustrating the absolute value of the angular velocity difference value of the pitch angle $\Delta\omega_{Pitch}^{P,car}$ is larger than the threshold $\omega_P$ and exceeds a certain frequency f. As long as the relationship between the angular velocity of the driver and the frequency in FIG. 5A~5C meets at least one of cases, it is determined that distracted driving, and the message is issued to alert the driver to concentrate.

In the present exemplary embodiment, information and data transmitted by the first electrical device 110 are sent by the micro-controller 170 through the communication unit 130A, and information and data transmitted by the second electrical device 210 are sent by the micro-controller 180 through the communication unit 130B. Each of the communication units 130A and 130B has automatic connection feature, and therefore the user can easily operate and use the first electrical device 110 and the second electrical device 210. Here, each of the communication units 130A and 130B may support a wireless signal transmission technique such as global system for mobile communications (GSM), the third generation (3G) mobile communication, 4G mobile communication, long terminal evolution (LTE) network, personal handyphone system (PHS), code division multiple access (CDMA), wireless fidelity (Wi-Fi), worldwide interoperability for microwave access (WiMAX), Bluetooth, etc. In another exemplary embodiment, each of the communication units 130A and 130B may also support a wired signal transmission technique, for example, universal serial bus (USB), Firewire serial interface or a Thunderbolt serial interface. In the present exemplary embodiment, the communication unit 130A of the first electrical device 110 is used for connecting to the communication unit 130B of the second electrical device 210 and the remote server.

In summary, according to the method and the system for detecting conditions of drivers and electronic apparatus provide by the disclosure, a sensor of the vehicle side detects the absolute vehicle angle and the sensor of the driver side detects the absolute head angle, then the regulation process and detecting distracted driving may be performed. When the posture of the driver's head maintains for a long time or the driver's head frequently turns, the message is issued automatically to alert the driver to avoid or reduce traffic risks.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A system for detecting a condition of a driver, the system comprising:
   a first electrical device, including a first sensor coupling to a first communication unit, wherein the first sensor is configured to detect an initial vehicle angle of a vehicle on a first dimension;
   a second electrical device, including a second sensor coupling to a second communication unit, wherein the second sensor is configured to detect an initial head angle of the driver on the first dimension;
   a regulation unit, disposed in the first electrical device or the second electrical device, calculating a regulation angle on the first dimension based on the initial vehicle angle and the initial head angle on the first dimension; and an alert unit, disposed in the first electrical device or the second electrical device, wherein the first sensor detects a current vehicle angle of the vehicle on the first dimension, and the second sensor detects a current head angle of the driver on the first dimension, wherein the regulation unit calculates a regulated head angle of the driver on the first dimension based on the current head angle and the regulation angle on the first dimension, wherein the alert unit calculates the absolute value of a difference value on the first dimension between the current vehicle angle and the regulated head angle on the first dimension and determines whether the absolute value of the difference value on the first dimension is larger than a first threshold, if the absolute value of the difference value on the first dimension is larger than the first threshold, the alert unit generates a warning message.

2. The system as claimed in claim 1, wherein the warning message comprises at least one of a voice, a video, a vibration or a combination thereof.

3. The system as claimed in claim 1, wherein the first sensor is configured to detect a current vehicle speed of the vehicle, and determines whether the current vehicle speed is larger than a vehicle speed threshold, wherein the alert unit generates the warning message when the absolute value of the difference value on the first dimension is larger than the first threshold and the current vehicle speed is larger than the vehicle speed threshold.

4. The system as claimed in claim 3, wherein the first sensor further comprising:

a speed sensor, detecting the current vehicle speed; and
an angle sensor, detecting the initial vehicle angle and the current vehicle angle on the first dimension.

5. The system as claimed in claim 1, wherein the first sensor detects an initial vehicle angle of the vehicle on a second dimension, and the second sensor detects an initial head angle of the driver on the second dimension, wherein the regulation unit calculates a regulation angle on the second dimension based on the initial vehicle angle and the initial head angle on the second dimension, wherein the first sensor detects a current vehicle angle of the vehicle on the second dimension, and the second sensor detects a current head angle of the driver on the second dimension, wherein the regulation unit calculates a regulated head angle of the driver on the second dimension based on the current head angle and the regulation angle on the second dimension, wherein the alert unit calculates the absolute value of a difference value on the second dimension between the current vehicle angle and the regulated head angle on the second dimension and determines whether the absolute value of the difference value on the second dimension is larger than a second threshold, if the absolute value of the difference value on the second dimension is larger than the second threshold, the alert unit generates the warning message.

6. The system as claimed in claim 5, wherein the first sensor detects an initial vehicle angle of the vehicle on a third dimension, and the second sensor detects an initial head angle of the driver on the third dimension, wherein the regulation unit calculates a regulation angle on the third dimension based on the initial vehicle angle and the initial head angle on the third dimension, wherein the first sensor detects a current vehicle angle of the vehicle on the third dimension, and the second sensor detects a current head angle of the driver on the third dimension, wherein the regulation unit calculates a regulated head angle of the driver on the third dimension based on the current head angle and the regulation angle on the third dimension, wherein the alert unit calculates the absolute value of a difference value on the third dimension between the current vehicle angle and the regulated head angle on the third dimension and determines whether the absolute value of the difference value on the third dimension is larger than a third threshold, if the absolute value of the difference value on the third dimension is larger than the third threshold, the alert unit generates the warning message.

7. The system as claimed in claim 1, wherein the alert unit further calculates a predetermined time, if the absolute value of the difference value on the first dimension is larger than the first threshold for the predetermined time, the alert unit generates the warning message.

8. The system as claimed in claim 1, further comprising:
a remote server, wherein the alert unit transmits the warning message to the remote server through the first communication unit or the second communication unit.

9. The system as claimed in claim 1, wherein each of the first sensor and the second sensor is a compass or a magnetometer.

10. The system as claimed in claim 1, wherein each of the first communication unit and the second communication unit is a wireless communication unit or a wired communication unit.

11. An electronic apparatus, comprising:
a micro-controller;
a sensor, coupled to the micro-controller and configured to detect an initial angle and a current angle of the electronic apparatus on a first dimension;
a communication unit, coupled to the micro-controller and configured to receive a first signal of an initial angle of an another electronic apparatus on the first dimension, and receives a second signal of a current angle of the another electronic apparatus on the first dimension;
a regulation unit, coupled to the micro-controller, wherein the regulation unit calculates a regulation angle on the first dimension based on the initial angle of the electronic apparatus on the first dimension and the initial angle of the another electronic apparatus on the first dimension, and adjusts one of the current angle of the electronic apparatus on the first dimension and the current angle of the another electronic apparatus on the first dimension based on the regulation angle on the first dimension to generate a regulated angle on the first dimension; and
an alert unit, coupled to the micro-controller, wherein the alert unit calculates the absolute value of a difference value on the first dimension between the regulated angle on the first dimension and another one of the current angle of the electronic apparatus on the first dimension and the current angle of the another electronic apparatus on the first dimension and determines whether the absolute value of the difference value on the first dimension is larger than a first threshold, if the absolute value of the difference value on the first dimension is larger than the first threshold, the alert unit generates a warning message.

12. The apparatus as claimed in claim 11, wherein the warning message comprises at least one of a voice, a video, a vibration or a combination thereof.

13. The apparatus as claimed in claim 11, wherein the sensor is configured to detects a current vehicle speed of a vehicle, and determines whether the current vehicle speed is larger than a vehicle speed threshold,
wherein the alert unit generates the warning message only when the absolute value of the difference value on the first dimension is larger than the first threshold and the current vehicle speed is larger than the vehicle speed threshold.

14. The apparatus as claimed in claim 13, wherein the sensor further comprising:
a speed sensor, detecting the current vehicle speed; and
an angle sensor, detecting the initial angle of the vehicle on the first dimension and the current angle of the vehicle on the first dimension.

15. The apparatus as claimed in claim 11, wherein the sensor detects an initial angle of the electronic apparatus on a second dimension, and the communication unit receives an initial angle of the another electronic apparatus on the second dimension,
wherein the regulation unit calculates a regulation angle on the second dimension based on the initial angle of the electronic apparatus on the second dimension and the initial angle of the another electronic apparatus on the second dimension,
wherein the sensor detects a current angle of the electronic apparatus on the second dimension, and the communication unit receives a current angle of the another electronic apparatus on the second dimension,
wherein the regulation unit adjusts one of the current angle of the electronic apparatus on the second dimension and the current angle of the another electronic apparatus on the second dimension based on the regulation angle on the second dimension to generate a regulated angle on the second dimension,
wherein the alert unit calculates the absolute value of a difference value on the second dimension between the regulated angle on the second dimension and another one of the current angle of the electronic apparatus on the second dimension and the current angle of the another electronic apparatus on the second dimension and determines whether the absolute value of the difference value on the second dimension is larger than a second threshold,
if the absolute value of the difference value on the second dimension is larger than the second threshold, the alert unit generates the warning message.

16. The apparatus as claimed in claim 15, wherein the sensor detects an initial angle of the electronic apparatus on a third dimension, and the communication unit receives an initial angle of the another electronic apparatus on the third dimension,
wherein the regulation unit calculates a regulation angle on the third dimension based on the initial angle of the electronic apparatus on the third dimension and the initial angle of the another electronic apparatus on the third dimension,
wherein the sensor detects a current angle of the electronic apparatus on the third dimension, and the communication unit receives a current angle of the another electronic apparatus on the third dimension,
wherein the regulation unit adjust one of the current angle of the electronic apparatus on the third dimension and the current angle of the another electronic apparatus on the third dimension based on the regulation angle on the third dimension to generate a regulated angle on the third dimension,
wherein the alert unit calculates the absolute value of a difference value on the third dimension between the regulated angle on the third dimension and another one of the current angle of the electronic apparatus on the third dimension and the current angle of the another electronic apparatus on the third dimension and determines whether the absolute value of the difference value on the third dimension is larger than a third threshold,
if the absolute value of the difference value on the third dimension is larger than the third threshold, the alert unit generates the warning message.

17. The apparatus as claimed in claim 11, wherein the alert unit further calculates a predetermined time, if the absolute value of the difference value on the first dimension is larger than the first threshold for the predetermined time, the alert unit generates the warning message.

18. The apparatus as claimed in claim 11, wherein the alert unit transmits the warning message to a remote server through the communication.

19. The apparatus as claimed in claim 11, wherein the sensor is a compass or a magnetometer.

20. The apparatus as claimed in claim 11, wherein the communication unit is a wireless communication unit or a wired communication unit.

21. A method for detecting a condition of a driver, the method comprising:
detecting an initial vehicle angle of a vehicle on a first dimension;
detecting an initial head angle of the driver on the first dimension;
reading a regulation signal to determine whether to perform a regulation process, and when reading the regulation signal, calculating a regulation angle on the first dimension based on the initial head angle and the initial vehicle angle on the first dimension;
detecting a current vehicle angle of the vehicle on the first dimension and a current head angle of the driver on the first dimension;
calculating a regulated head angle of the driver on the first dimension based on the current head angle and the regulation angle on the first dimension;
calculating the absolute value of a difference value between the current vehicle angle and the regulated head angle on the first dimension;
determining whether the absolute value of the difference value on the first dimension is larger than a first threshold; and
generating a warning message, if the absolute value of the difference value on the first dimension is larger than the first threshold.

22. The method as claimed in claim 21, wherein the step of generating a warning message comprising:
generating at least one of a voice, a video, a vibration or a combination of the voice, the video, and the vibration.

23. The method as claimed in claim 21, the method further comprising:
detecting a current vehicle speed of the vehicle;
determining whether the current vehicle speed is larger than a vehicle speed threshold; and
executing the step of generating the warning message when the absolute value of the difference value on the first dimension is larger than the first threshold and the current vehicle speed is larger than the vehicle speed threshold.

24. The method as claimed in claim 21, the method further comprising:
detecting an initial vehicle angle of the vehicle on second dimension;
detecting an initial head angle of the driver on second dimension;
calculating a regulation angle on the second dimension based on the initial head angle and the initial vehicle angle on the second dimension;
detecting a current vehicle angle of the vehicle on the second dimension and a current head angle of the driver on the second dimension;
calculating a regulated head angle of the driver on the second dimension based on the current head angle and the regulation angle on the second dimension;
calculating the absolute value of a difference value on the second dimension between the current vehicle angle and the regulated head angle on the second dimension;
determining whether the absolute value of the difference value on the second dimension is larger than a second threshold; and
generating the warning message, if the absolute value of the difference value on the second dimension is larger than the second threshold.

25. The method as claimed in claim 24, the method further comprising:
detecting an initial vehicle angle of the vehicle on a third dimension;
detecting an initial head angle of the driver on the third dimension;
calculating a regulation angle on the third dimension based on the initial head angle and the initial vehicle angle on the third dimension;
detecting a current vehicle angle of the vehicle on the third dimension and a current head angle of the driver on the third dimension;
calculating a regulated head angle of the driver on the third dimension based on the current head angle and the regulation angle on the third dimension;
calculating the absolute value of a difference value on the third dimension between the current vehicle angle and the regulated head angle on the third dimension;
determining whether the absolute value of the difference value on the third dimension is larger than a third threshold; and
generating the warning message, if the absolute value of the difference value on the third dimension is larger than the third threshold.

26. The method as claimed in claim 21, the method further comprising:
calculating a predetermined time; and
executing the step of generating the warning message, if the absolute value of the difference value on the first dimension is larger than the first threshold for the predetermined time.

27. The method as claimed in claim 21, the method further comprising:
transmitting the warning message to a remote server.

28. A system for detecting a condition of a driver, the system comprising:
a first electrical device, including a first sensor coupling to a first communication unit, wherein the first sensor is configured to detect an initial vehicle angular velocity of a vehicle on a first dimension;
a second electrical device, including a second sensor coupling to a second communication unit, wherein the second sensor is configured to detect an initial head angular velocity of the driver on the first dimension;
a regulation unit, disposed in the first electrical device or the second electrical device, wherein the regulation unit is configured to calculate a regulation angular velocity on the first dimension based on the initial vehicle angular velocity and the initial head angular velocity on the first dimension; and
an alert unit, disposed in the first electrical device or the second electrical device,
wherein the first sensor detects a current vehicle angular velocity of the vehicle on the first dimension, and the second sensor detects a current head angular velocity of the driver on the first dimension,
wherein the regulation unit calculates a regulated head angular velocity of the driver on the first dimension based on the current head angular velocity and the regulation angular velocity on the first dimension,
wherein the alert unit calculates the absolute value of an angular velocity difference value on the first dimension between the current vehicle angular velocity and the regulated head angular velocity on the first dimension and determines whether the absolute value of the angular velocity difference value on the first dimension is larger than a first threshold,
if the absolute value of the angular velocity difference value on the first dimension is larger than the first threshold, the alert unit generates a warning message.

29. An electronic apparatus, comprising:
a micro-controller;
a sensor, coupled to the micro-controller and configured to detect an initial angular velocity and a current angular velocity of the electronic apparatus on a first dimension;
a communication unit, coupled to the micro-controller and configured to receive a first signal of an initial angular velocity of an another electronic apparatus on the first dimension, and receives a second signal of a current angular velocity of the another electronic apparatus on the first dimension;
a regulation unit, coupled to the micro-controller, wherein the regulation unit calculates a regulation angular velocity on the first dimension based on the initial angular velocity of the electronic apparatus on the first dimension and the initial angular velocity of the another electronic apparatus on the first dimension, and adjusts one of the current angular velocity of the electronic apparatus on the first dimension and the current angular velocity of the another electronic apparatus on the first dimension based on the regulation angular velocity to generate a regulated angular velocity on the first dimension; and
an alert unit, coupled to the micro-controller, wherein the alert unit calculates the absolute value of an angular velocity difference value on the first dimension between the regulated angular velocity on the first dimension and another one of the current angular velocity of the electronic apparatus on the first dimension and the current angular velocity of the another electronic apparatus on the first dimension and determines whether the absolute value of the angular velocity difference value one the first dimension is larger than a first threshold,
if the absolute value of the angular velocity difference value on the first dimension is larger than the first threshold, the alert unit generates a warning message.

30. A method for detecting a condition of a driver, the method comprising:

detecting an initial vehicle angular velocity of a vehicle on a first dimension;

detecting an initial head angular velocity of the driver on the first dimension;

reading a regulation signal to determine whether to perform a regulation process, and when reading the regulation signal, calculating a regulation angular velocity on the first dimension based on the initial head angular velocity and the initial vehicle angular velocity on the first dimension;

detecting a current vehicle angular velocity of the vehicle on the first dimension and a current head angular velocity of the driver on the first dimension;

calculating a regulated head angular velocity of the driver on the first dimension based on the current head angular velocity and the regulation angular velocity on the first dimension;

calculating the absolute value of an angular velocity difference value on the first dimension between the current vehicle angular velocity and the regulated head angular velocity on the first dimension;

determining whether the absolute value of the angular velocity difference on the first dimension value is larger than a first threshold; and generating a warning message, if the absolute value of the angular velocity difference value on the first dimension is larger than the first threshold.

* * * * *